(12) United States Patent
Ueda et al.

(10) Patent No.: US 11,116,958 B2
(45) Date of Patent: Sep. 14, 2021

(54) CONNECTOR

(71) Applicant: TERUMO KABUSHIKI KAISHA, Tokyo (JP)

(72) Inventors: Yasuhiro Ueda, Kofu (JP); Takeshi Toyama, Minami-Alps (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 93 days.

(21) Appl. No.: 16/231,361

(22) Filed: Dec. 21, 2018

(65) Prior Publication Data

US 2019/0117953 A1 Apr. 25, 2019

Related U.S. Application Data

(63) Continuation of application No. PCT/JP2017/023361, filed on Jun. 26, 2017.

(30) Foreign Application Priority Data

Jun. 24, 2016 (JP) .............................. JP2016-125768

(51) Int. Cl.
*A61M 39/26* (2006.01)
*A61M 39/10* (2006.01)
(Continued)

(52) U.S. Cl.
CPC ........ *A61M 39/26* (2013.01); *A61M 39/1011* (2013.01); *A61M 39/20* (2013.01);
(Continued)

(58) Field of Classification Search
CPC ............ A61M 39/26; A61M 2039/205; A61M 2039/261; A61M 2039/266; A61M 2039/1072

See application file for complete search history.

(56) References Cited

U.S. PATENT DOCUMENTS

| 5,085,645 A * | 2/1992 | Purdy | .................... | A61M 39/26 604/167.03 |
| 5,569,235 A * | 10/1996 | Ross | ..................... | A61M 39/26 251/149.1 |

(Continued)

FOREIGN PATENT DOCUMENTS

| JP | 2002-035140 A | 2/2002 |
| JP | 2002-355318 A | 12/2002 |

(Continued)

OTHER PUBLICATIONS

International Search Report with English language translation and Written Opinion issued in International Application No. PCT/JP2017/023361 dated Aug. 1, 2017.

(Continued)

*Primary Examiner* — Emily L Schmidt
(74) *Attorney, Agent, or Firm* — Foley & Lardner LLP

(57) ABSTRACT

A connector includes: a housing that includes a tubular body connecting unit to which a tubular body is connectable, a concave portion inside the housing, and a receiving portion; and a valve body configured such that, when the tubular body is connected to the tubular body connecting unit, the valve body is pressed by the tubular body against a biasing force, thereby sliding from a closed position to an opened position. The valve body includes an overriding portion configured such that, as the valve body slides from a closed position side toward an opened position side, the overriding portion is pressed against the receiving portion of the housing and rides over the receiving portion by elastic deformation.

15 Claims, 7 Drawing Sheets

(51) Int. Cl.
*A61M 39/20* (2006.01)
*A61M 39/22* (2006.01)

(52) U.S. Cl.
CPC ........... *A61M 2039/1033* (2013.01); *A61M 2039/229* (2013.01); *A61M 2039/266* (2013.01); *A61M 2205/0216* (2013.01)

(56) References Cited

U.S. PATENT DOCUMENTS

| | | | |
|---|---|---|---|
| 5,782,816 A * | 7/1998 | Werschmidt | A61M 39/02 604/256 |
| 2006/0163515 A1 | 7/2006 | Ruschke | |
| 2011/0282302 A1 * | 11/2011 | Lopez | A61M 39/16 604/247 |

FOREIGN PATENT DOCUMENTS

| | | |
|---|---|---|
| JP | 2008-540045 A | 11/2008 |
| JP | 2015-142833 A | 8/2015 |
| WO | WO-2015/145998 A1 | 10/2015 |
| WO | WO-2016/047135 A1 | 3/2016 |

OTHER PUBLICATIONS

Office Action dated Jan. 5, 2021 in related Japanese Patent Application No. 2018-523715.

* cited by examiner

CONNECTOR

CROSS-REFERENCE TO RELATED APPLICATIONS

The present application is a bypass continuation of PCT Appl. No. PCT/JP2017/023361, filed on Jun. 26, 2017, which claims priority to Japanese Appl. No. 2016-125768, filed on Jun. 24, 2016. The contents of these disclosures are hereby incorporated by reference in their entireties.

BACKGROUND

The present disclosure relates to a connector provided with a valve body that is slidable on an inner peripheral surface of an accommodating concave portion defined inside a housing.

Conventionally, for example, a connector for connecting members for forming a flow path of fluid is used in a medical infusion device, a body fluid sampling device or the like. In one such known connector, a connector provided with a housing defining an internal flow path and a valve body capable of interrupting communication between the internal flow path and an outside of the housing.

As disclosed in, for example, PCT Pub. No. WO2015/145998, such a connector is configured such that the valve body slides on an inner peripheral surface of an accommodating concave portion defined inside the housing from a closed position in which the communication between the internal flow path and the outside of the housing is interrupted to an opened position in which the internal flow path is allowed to communicate with a lumen of the tubular body by being pressed by the tubular body against biasing force when the tubular body is connected to the tubular body connecting unit of the housing.

According to such a configuration, it is possible to inhibit fluctuation in internal flow path volume due to connection/separation operation of the tubular body to/from the connector, thereby realizing a connector that is less susceptible to cause unintentional extrusion of chemical liquid to a living body and unintentional pulling of body fluid from the living body when the connector is connected/separated.

SUMMARY

However, in the connector of the conventional configuration described above, depending on a shape of a surface of the valve body facing the internal flow path in the closed position, when pressure in the internal flow path increases, there is a risk that the valve body moves toward the opened position by the increased pressure, whereby the fluid leaks.

Certain embodiments of the present disclosure have been developed to solve such a problem, and one object thereof is to provide a connector capable of inhibiting occurrence of fluid leakage when the internal pressure increases.

In one embodiment, a connector includes: a housing including a tubular body connecting unit to which a tubular body may be connected and defining an internal flow path communicated with a lumen of the tubular body connected to the tubular body connecting unit and an accommodating concave portion inside the housing; and a valve body pressed by the tubular body against biasing force in accordance with connection of the tubular body to the tubular body connecting unit, thereby sliding on an inner peripheral surface of the accommodating concave portion from a closed position in which communication of the internal flow path with an outside of the housing is interrupted to an opened position in which the internal flow path is allowed to communicate with the lumen of the tubular body, in which the valve body is provided with an overriding portion that is pressed against a receiving portion provided on the housing and rides over the receiving portion by elastic deformation as the valve body slides from a closed position side toward an opened position side.

In one aspect, the overriding portion abuts the receiving portion in the closed position of the valve body.

In one aspect, the valve body is provided with an annular seal portion that slides on the inner peripheral surface of the accommodating concave portion from the closed position to the opened position.

In one aspect, the receiving portion is formed on the inner peripheral surface of the accommodating concave portion, and the overriding portion is formed in an annular shape and configured to serve as the seal portion.

In one aspect, the overriding portion is an annular convex portion, and the receiving portion is an annular stepped portion.

In one aspect, the valve body is provided with a pressing portion that is pressed against a second receiving portion provided on the housing as the valve body slides from the opened position to the closed position.

In one aspect, the pressing portion abuts the second receiving portion in the closed position of the valve body.

In one aspect, the tubular body connecting unit includes a connecting opening into which the tubular body may be fitted, the second receiving portion is formed on an inner peripheral surface continuous to the connecting opening, and the pressing portion is configured to serve as an annular seal portion that abuts the second receiving portion in a liquid-tight manner in the closed position of the valve body.

In one aspect, the pressing portion is an annular convex portion, and the second receiving portion is an annular stepped portion.

In one aspect, the pressing portion is movable to an inside of the accommodating concave portion as the valve body slides to the opened position, each of the pressing portion and the overriding portion is an annular convex portion, and a circumference of the pressing portion is smaller than a circumference of the overriding portion.

In one aspect, the circumference of the pressing portion is smaller than a circumference of the inner peripheral surface of the accommodating concave portion.

In one aspect, a spring body that applies biasing force from the opened position side toward the closed position side to the valve body is arranged in the accommodating concave portion.

In one aspect, a valve member made of an elastic material integrally including the valve body and the spring body is provided.

v, the housing is formed of a cap member including the tubular body connecting unit and a holder member including the accommodating concave portion, and the internal flow path includes a space defined between the cap member and the holder member.

According to certain embodiments of the present disclosure, it is possible to provide a connector capable of inhibiting occurrence of leakage of fluid when the internal pressure increases.

DETAILED DESCRIPTION

Hereinafter, a connector 1 according to an embodiment of the present disclosure and several variations thereof will be described in detail by way of example with reference to FIGS. 1 to 8. In this specification, a vertical direction means a direction along a central axis O of an inner peripheral surface 13a of an accommodating concave portion 13, an upper side means an opening side of the accommodating concave portion 13 (upper side in FIG. 2), and a lower side means a bottom surface 13b side of the accommodating concave portion 13 (lower side in FIG. 2).

Figure 1:
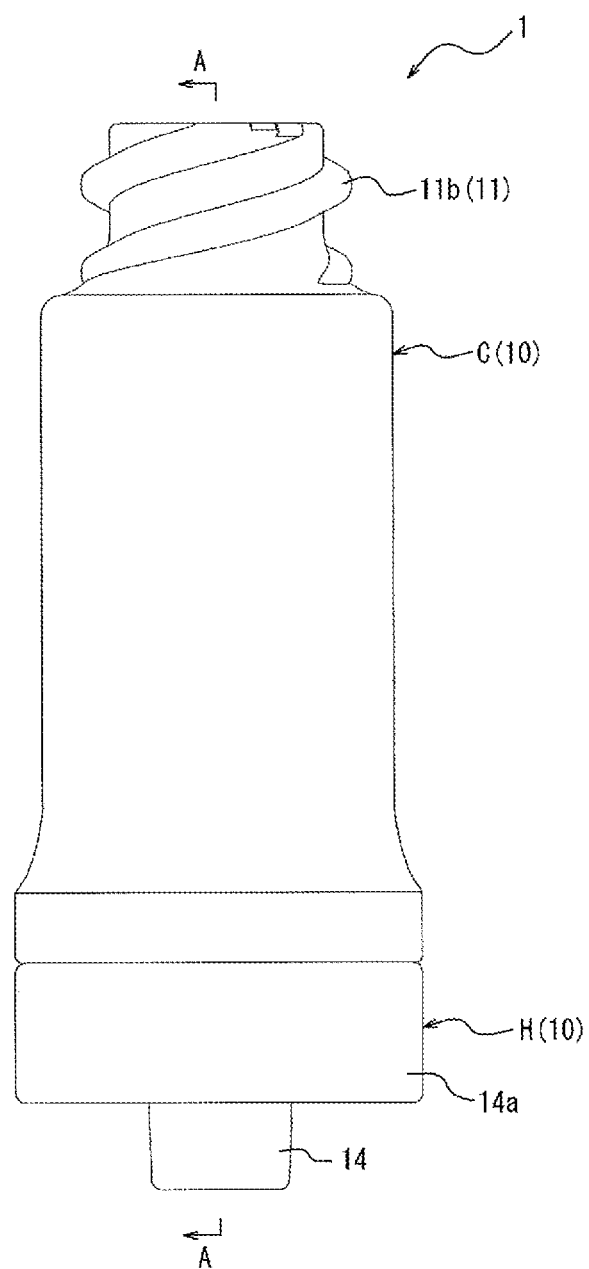
FIG. 1 is a side view of a connector according to an embodiment of the present invention.
Figure 2:
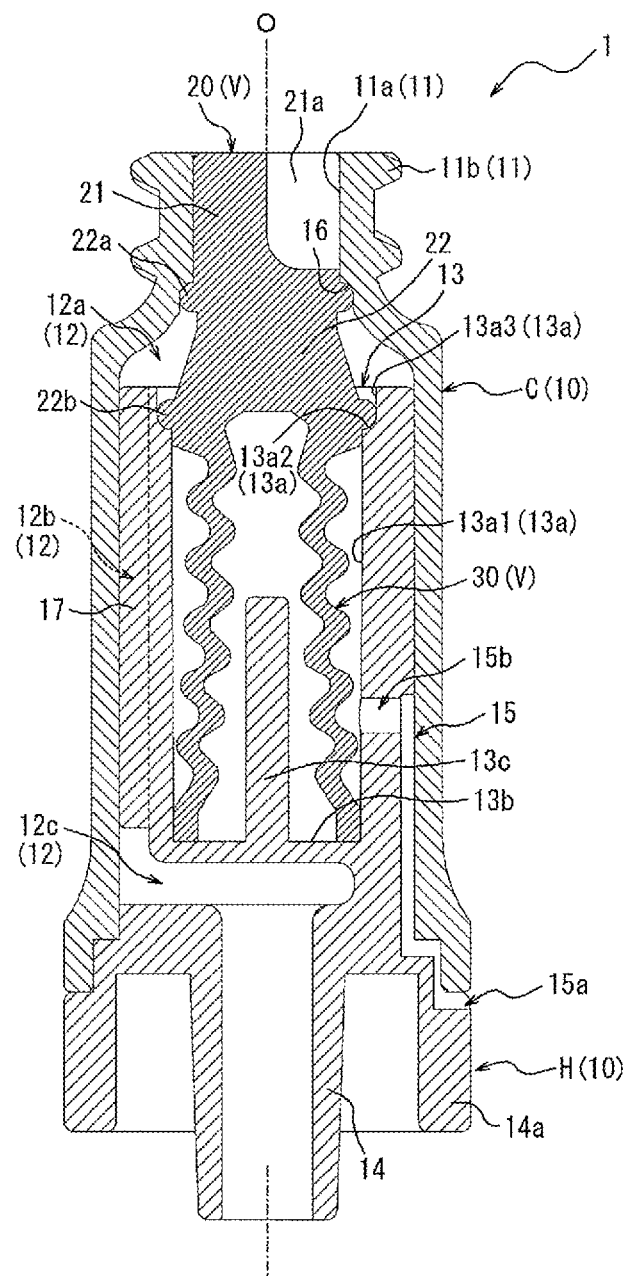
FIG. 2 is a cross-sectional view taken along line A-A of FIG. 1.
Figure 3:
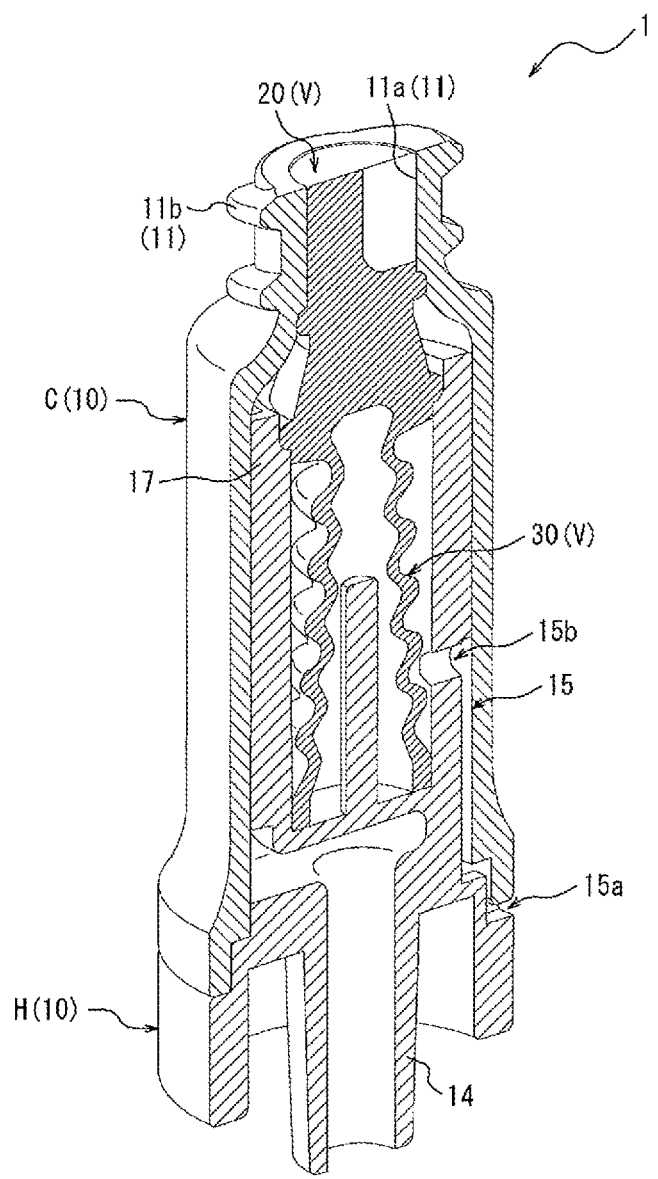
FIG. 3 is a cross-sectional perspective view of the connector illustrating a cross-section of FIG. 2.
Figure 6:
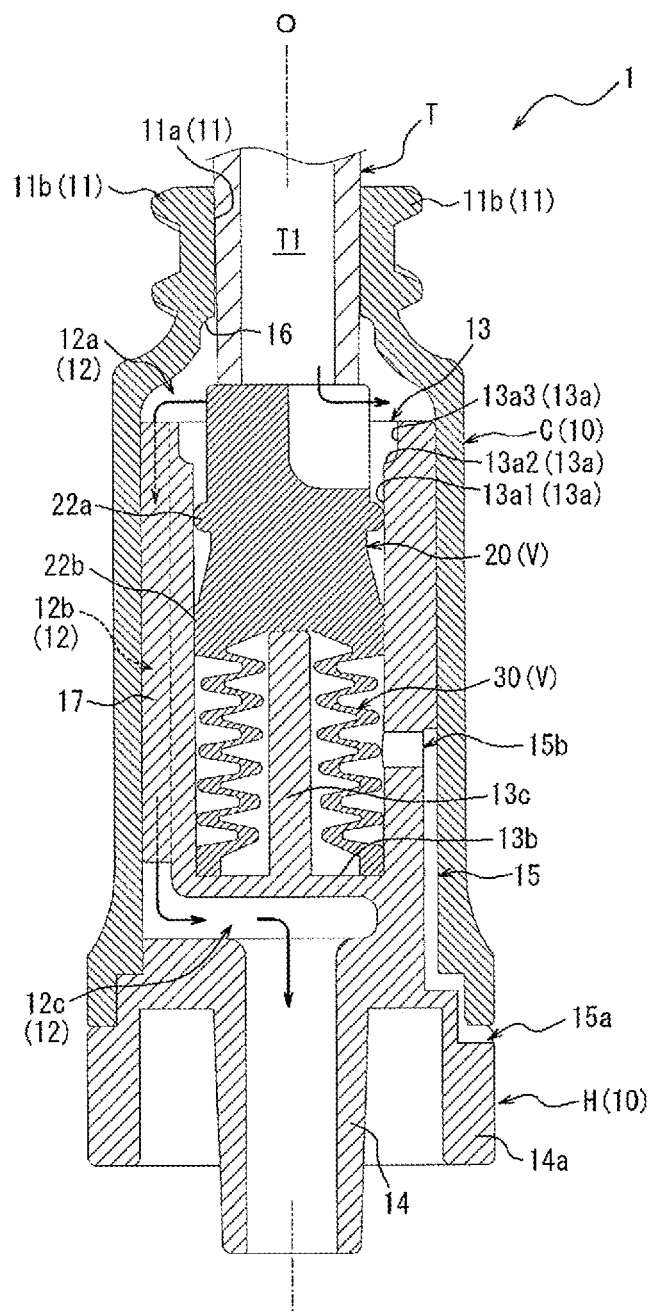
FIG. 6 is a cross-sectional view illustrating a state in which a tubular body is connected to the connector according to an embodiment of the present invention according to FIG. 2.

As illustrated in FIGS. 1 to 3, the connector 1 according to this embodiment is provided with a housing 10 and a valve body 20. As illustrated in FIG. 6, the housing 10 includes a tubular body connecting unit 11 to which a tubular body T may be connected and defines an internal flow path 12 communicated with a lumen T1 of the tubular body T connected to the tubular body connecting unit 11 and the accommodating concave portion 13 inside thereof. A spring body 30 arranged in the accommodating concave portion 13 applies biasing force from an opened position side to a closed position side (that is, from the lower side to the upper side in FIG. 6) to the valve body 20.

The valve body 20 and the spring body 30 form a part of a valve member V made of an elastic material such as rubber and thermoplastic elastomer, for example. That is, the connector 1 is provided with the valve member V made of the elastic material integrally including the valve body 20 and the spring body 30. The valve body 20 and the spring body 30 may be formed separately. The spring body 30 may be formed as a coil spring made of resin or metal.

The housing 10 is formed of a cap member C including the tubular body connecting unit 11 and a holder member H including the accommodating concave portion 13, and the internal flow path 12 includes a space defined between the cap member C and the holder member H. The housing 10 is not limited to that formed of the two members; this may also be formed of three or more members or a single member. The members for forming the housing 10 such as the cap member C and the holder member H may be made of synthetic resin, for example.

The housing 10 is provided with a connecting tubular body 14 that is connectable to another connector on an end on a side opposite to the tubular body connecting unit 11. The connecting tubular body 14 is formed as a lure lock type male lure. A female screw (not illustrated) for lure locking is formed on an inner peripheral surface of a tubular portion 14a surrounding the connecting tubular body 14. A lumen of the connecting tubular body 14 includes the second end of the internal flow path 12 located on a side opposite to a first end of the internal flow path 12 that may be closed by the valve body 20.

The connector 1 according to this embodiment is formed as a plug type connector provided with the tubular body connecting unit 11 and a single connecting tubular body 14. However, the connector 1 may also be formed as a Y-shaped connector or a T-shaped connector further provided with another connecting unit (a connecting unit for a tubular body or a connecting unit in a tubular body shape) communicated with the internal flow path 12 or this may also be formed as a three-way stopcock to which a flow path switching function is further added. Instead of providing the connecting tubular body 14, the connector 1 may instead be formed as an integrated connector provided integrally with an indwelling needle that may be indwelled in a living body or another medical device.

The tubular body connecting unit 11 includes a connecting opening 11a having a cylindrical shape into which the tubular body T formed as a lure slip type male lure may be fitted. The tubular body connecting unit 11 also includes a male screw 1ib that allows the tubular body formed as the lure lock type male lure to be screwed. The male screw 1ib of the tubular body connecting unit 11 may also be omitted. In place of or in addition to such a configuration, the tubular body connecting unit 11 may include an engaging unit with the tubular body for connecting a tubular body of another configuration.

The valve body 20 is configured to slide on an inner peripheral surface 13a of the accommodating concave portion 13 from a closed position (refer to FIG. 2) in which the communication of the internal flow path 12 with an outside of the housing 10 is interrupted to an opened position (refer to FIG. 6) in which the internal flow path 12 is allowed to communicate with the lumen T1 of the tubular body T as this is pressed by the tubular body T against biasing force of the spring body 30 in accordance with the connection of the tubular body T formed as the male lure to the tubular body connecting unit 11. The valve body 20 may also be configured to perform a similar operation when a tubular body of another configuration (that is, other than the male lure) is connected to the tubular body connecting unit 11.

Figure 4:
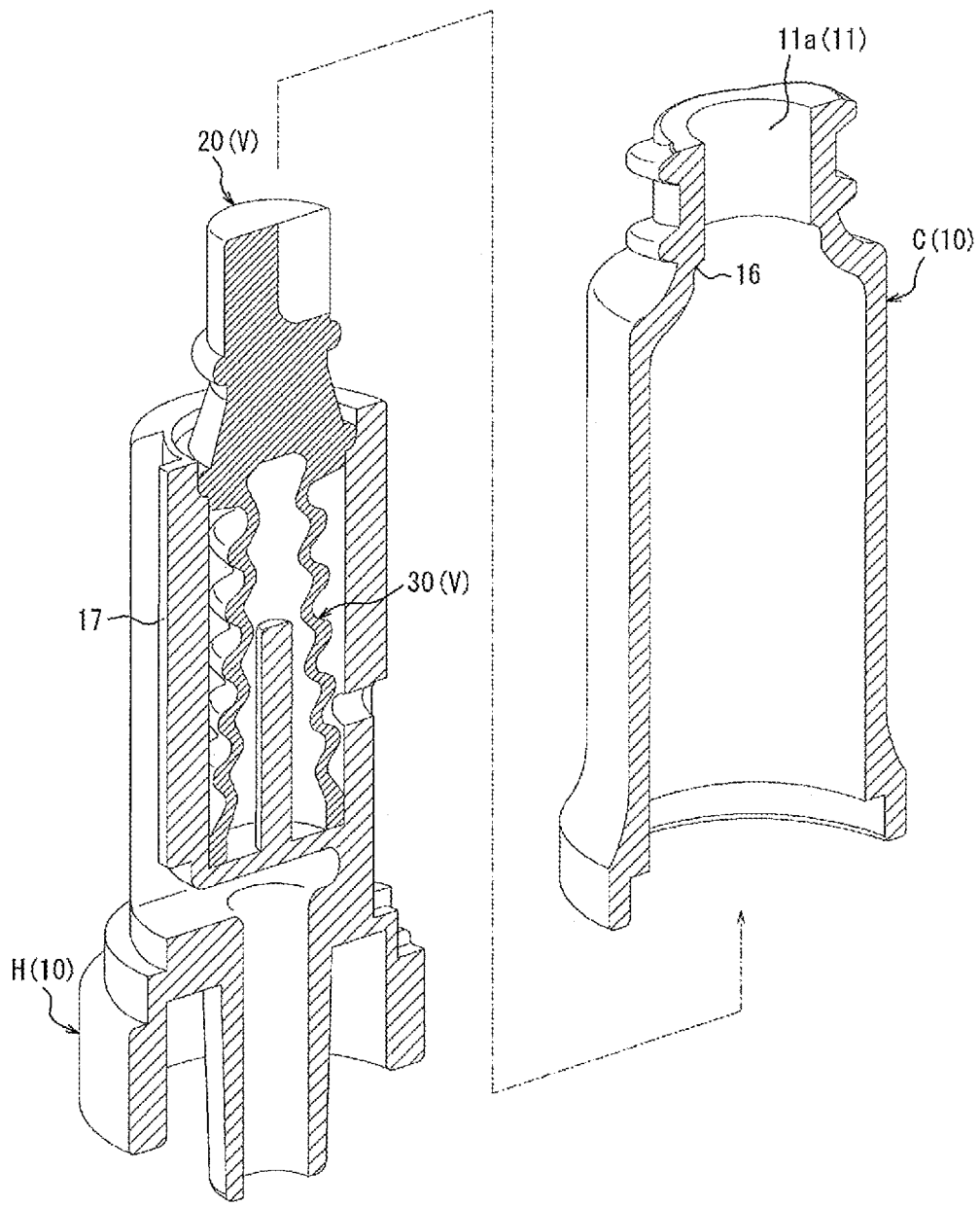
FIG. 4 is an exploded perspective view of the connector illustrating the state in FIG. 3 with a cap member separated.
Figure 5:
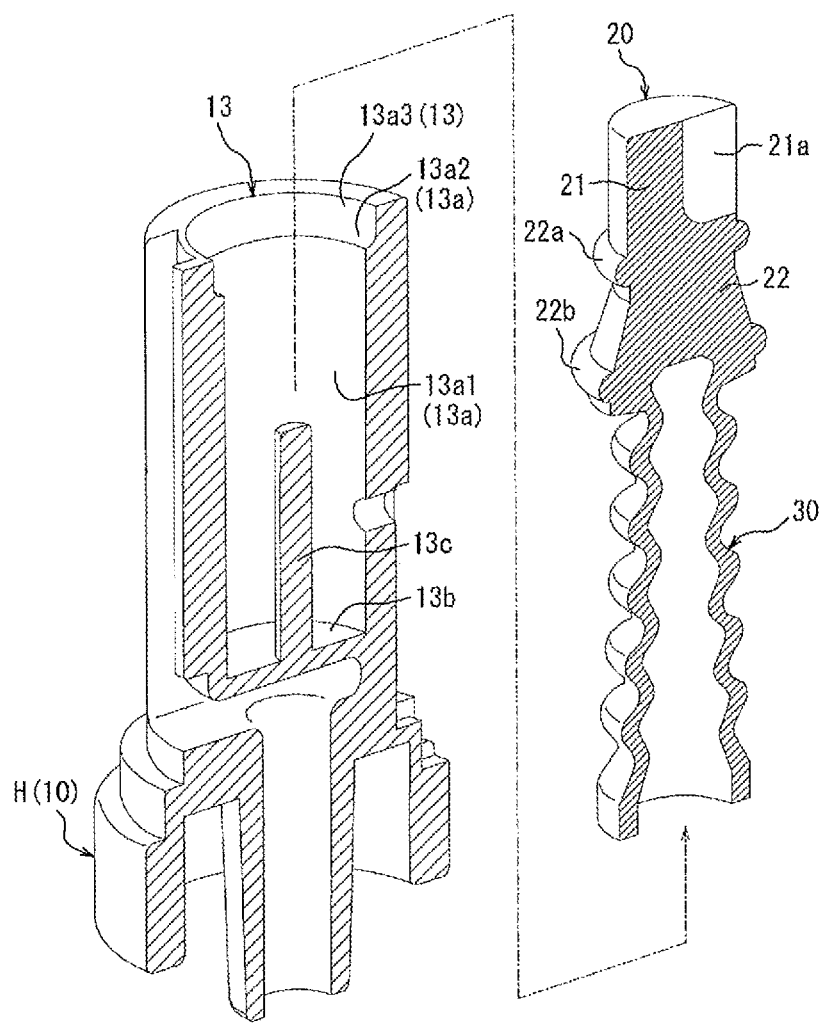
FIG. 5 is an exploded perspective view of the connector illustrating the state in FIG. 4 with a valve member separated.

As illustrated in FIGS. 2 to 5, the valve body 20 includes a cylindrical head portion 21 capable of closing the connecting opening 11a and a substantially conical body portion 22 continuous to the head portion 21. FIGS. 3 to 5 illustrate only a first side of a cross-section of the connector 1. A second side is configured to be symmetrical with the configuration of the first side in a portion other than the male screw 11b.

A slit 21a closed when the valve body 20 is in the closed position and opened when the valve body 20 is in the opened position is formed on the head portion 21 of the valve body 20. A pressing portion 22a formed as a ring-shaped annular convex portion is formed on an upper end edge of the body portion 22. The pressing portion 22a has a semicircular cross-sectional shape in the vertical direction. An overriding portion 22b formed as a ring-shaped annular convex portion is formed in the vicinity of a lower end edge of the body portion 22. The overriding portion 22b has a semicircular cross-sectional shape in the vertical direction.

The spring body 30 is formed as a bellows-shaped hollow cylindrical body, and is arranged in the accommodating concave portion 13 in a state of being slightly compressed in the vertical direction so as to apply upward biasing force to the valve body 20 even when the valve body 20 is in the closed position. The spring body 30 is not limited to the bellows-shaped one and this may also be formed into various shapes as long as this may apply the upward biasing force to the valve body 20.

The accommodating concave portion 13 includes a substantially cylindrical inner peripheral surface 13a and a circular bottom surface 13b. The inner peripheral surface 13a is formed of a cylindrical small-diameter portion 13a1 continuous to the bottom surface 13b, a receiving portion 13a2 formed as a ring-shaped annular stepped portion expanding stepwise from an upper end edge of the small-diameter portion 13a1, and a cylindrical large-diameter portion 13a3 continuous to the receiving portion 13a2. The receiving portion 13a2 has a cross-sectional shape in the vertical direction in an arc shape conforming to a cross-sectional shape of a lower portion of the overriding portion 22b.

On the small-diameter portion 13a1 of the inner peripheral surface 13a of the accommodating concave portion 13, the second end 15b of a ventilation path 15 of which a first end 15a is connected to the outside of the connector 1 is opened. By providing such ventilation path 15, air may be discharged to the outside through the ventilation path 15 when the valve body 20 moves to the opened position, so that it is possible to reduce operation force required when the tubular body T is connected. It is also possible to omit the ventilation path 15.

A support column 13c extending upward is formed at the center of the bottom surface 13b of the accommodating concave portion 13. By providing such support column 13c, when the valve body 20 is pressed by the tubular body T to move to the opened position as illustrated in FIG. 6, the support column 13c and the tubular body T may compress the valve body 20 vertically to sufficiently open the slit 21a.

It is also possible to omit the support column 13c. For example, it is possible to omit the support column 13c by changing a shape of the slit 21a or setting the biasing force of the spring body 30 to be stronger so that the slit 21a opens even without the support column 13c. It is also possible to provide a concave groove extending in a radial direction on an upper surface of the head portion 21 of the valve body 20 in place of the slit 21a. The concave groove allows the lumen T1 of the tubular body T to communicate with the internal flow path 12 when the valve body 20 is pressed by the tubular body T to move to the opened position. In this case also, the support column 13c may be omitted.

It is also possible to provide the support column 13c in a position eccentric to the center of the bottom surface 13b, so that, when the valve body 20 is pressed by the tubular body T to move to the opened position, the valve body 20 is tilted due to abutment with the support column 13c, and the lumen T1 of the tubular body T is communicated with the internal flow path 12. In this case, it is not required to provide the slit 21a and the concave groove on the valve body 20.

As illustrated in FIGS. 2 to 4, on an inner peripheral surface continuous to the connecting opening 11a, a second receiving portion 16 formed as a ring-shaped annular stepped portion expanding stepwise from a lower end edge of the connecting opening 11a is formed. The second receiving portion 16 has a cross-sectional shape in the vertical direction in an arc shape conforming to a cross-sectional shape of an upper portion of the pressing portion 22a.

The internal flow path 12 is formed of an annular flow path 12a including a first end on a side of the valve body 20 of the internal flow path 12 and surrounding an outer peripheral surface of the body portion 22 of the valve body 20 in the closed position, a side flow path 12b located on an outer peripheral side of the accommodating concave portion 13 with a first end continuous to the annular flow path 12a, and an additional flow path 12c continuous to a second end of the side flow path 12b and including a second end of the internal flow path 12.

The side flow path 12b is divided into two parts by one support rib 17 extending in a flow path direction at the center in a circumferential direction of the side flow path 12b. The support rib 17 provided on the holder member H abuts the cap member C in a state in which the holder member H is press-fitted into the cap member C and serves as a supporting unit that secures a width in the radial direction of the side flow path 12b. The support rib 17 may also be provided on the cap member C side. It is also possible to omit the support rib 17.

As illustrated in FIGS. 2 and 6, in this embodiment, the overriding portion 22b is configured to be pressed against the receiving portion 13a2 provided on the housing 10 to ride over the receiving portion 13a2 by elastic deformation as the valve body 20 slides from the closed position side toward the opened position side. The overriding portion 22b abuts the receiving portion 13a2 in the closed position of the valve body 20. The overriding portion 22b is configured to serve as an annular seal portion that slides on the inner peripheral surface 13a of the accommodating concave portion 13 until the valve body 20 moves from the closed position to the opened position.

In this embodiment, the pressing portion 22a is configured to be pressed against the second receiving portion 16 provided on the housing 10 as the valve body 20 slides from the opened position to the closed position. The pressing portion 22a abuts the second receiving portion 16 in the closed position of the valve body 20. The pressing portion 22a is configured to serve as the annular seal portion that abuts the second receiving portion 16 in a liquid-tight manner in the closed position of the valve body 20.

The pressing portion 22a is movable to an inside of the accommodating concave portion 13 as the valve body 20 slides toward the opened position (refer to FIG. 6), and a circumference of the pressing portion 22a is smaller than a circumference of the overriding portion 22b. More specifically, the circumference of the pressing portion 22a is smaller than a circumference of the inner peripheral surface of the accommodating concave portion 13 (refer to FIG. 2).

As described above, the connector 1 according to this embodiment is provided with the housing 10 that includes the tubular body connecting unit 11 to which the tubular body T may be connected and defines the internal flow path 12 communicated with the lumen T1 of the tubular body T connected to the tubular body connecting unit 11 and the accommodating concave portion 13 inside thereof, and the valve body 20 that slides on the inner peripheral surface 13a of the accommodating concave portion 13 from the closed position, in which the communication of the internal flow path 12 with the outside of the housing 10 is interrupted, to the opened position in which the internal flow path 12 is allowed to communicate with the lumen T1 of the tubular body T by being pressed by the tubular body T against the biasing force as the tubular body T is connected to the tubular body connecting unit 11. The valve body 20 is provided with the overriding portion 22b pressed against the receiving portion 13a2 provided on the housing 10 to override the receiving portion 13*a*2 by elastic deformation as the valve body slides from the closed position side toward the opened position side.

Therefore, according to the connector 1 according to this embodiment, even in a case in which fluid pressure in the internal flow path 12 increases and the fluid pressure acts in a direction to slide the valve body 20 from the closed position side toward the opened position side, it is possible to generate resistance force to prevent the sliding of the valve body 20 by the engagement of the overriding portion 22*b* with the receiving portion 13*a*2 from when the overriding portion 22*b* of the valve body 20 is pressed against the receiving portion 13*a*2 of the housing 10 until this overrides the receiving portion 13*a*2 by elastic deformation, so that it is possible to inhibit the valve body 20 from sliding to the opened position to cause leakage of fluid.

In the connector 1 according to this embodiment, because the overriding portion 22*b* abuts the receiving portion 13*a*2 in the closed position of the valve body 20, occurrence of the fluid leakage when the fluid pressure in the internal flow path 12 increases may be advantageously inhibited.

In the connector 1 according to this embodiment, the valve body 20 is provided with the annular seal portion (formed of the overriding portion 22*b* in this embodiment) that slides on the inner peripheral surface 13*a* of the accommodating concave portion 13 from the closed position to the opened position, so that it is possible to inhibit occurrence of contamination due to the fluid in the internal flow path 12 entering and staying on the bottom surface 13*b* side of the accommodating concave portion 13.

In the connector 1 according to this embodiment, the receiving portion 13*a*2 is formed on the inner peripheral surface 13*a* of the accommodating concave portion 13, and the overriding portion 22*b* is formed to be annular to serve as the seal portion, so that it is possible to obtain a sealing function by a simple configuration.

In the connector 1 according to this embodiment, because the overriding portion 22*b* is the annular convex portion and the receiving portion 13*a*2 is the annular stepped portion, it is possible to effectively satisfy both the resistance force that prevents the valve body 20 from sliding when the internal pressure increases and the sealing function.

In the connector 1 according to this embodiment, the valve body 20 is provided with the pressing portion 22*a* that is pressed against the second receiving portion 16 provided on the housing 10 as the valve body 20 slides from the opened position to the closed position. Therefore, it is possible to inhibit occurrence of slip of the valve body 20 that the valve body 20 slips out of the housing 10 when the valve body 20 returns from the opened position to the closed position or the like.

In the connector 1 according to this embodiment, because the pressing portion 22*a* abuts the second receiving portion 16 in the closed position of the valve body 20, occurrence of the slip of the valve body 20 may be advantageously inhibited.

In the connector 1 according to this embodiment, the tubular body connecting unit 11 includes the connecting opening 11*a* into which the tubular body T may be fitted, the second receiving portion 16 is formed on the inner peripheral surface continuous to the connecting opening 11*a*, and the pressing portion 22*a* serves as the annular seal portion that abuts the second receiving portion 16 in a liquid-tight manner in the closed position of the valve body 20, so that it is possible to obtain the sealing function for inhibiting the occurrence of the fluid leakage by a simple configuration.

In the connector 1 according to this embodiment, because the pressing portion 22*a* is the annular convex portion and the second receiving portion 16 is the annular stepped portion, it is possible to effectively satisfy both the function of inhibiting the occurrence of the slip of the valve body 20 and the sealing function.

In the connector 1 according to this embodiment, the pressing portion 22*a* is movable to the inside of the accommodating concave portion 13 as the valve body 20 slides to the opened position, each of the pressing portion 22*a* and the overriding portion 22*b* is the annular convex portion, and the circumference of the pressing portion 22*a* is smaller than the circumference of the inner peripheral surface 13*a* of the accommodating concave portion 13, so that it is possible to avoid an increase in sliding resistance of the valve body 20 with respect to the accommodating concave portion 13 caused by the pressing portion 22*a*.

Even in a case in which the circumference of the pressing portion 22*a* is not made smaller than the circumference of the inner peripheral surface 13*a* of the accommodating concave portion 13, as long as the circumference of the pressing portion 22*a* is made smaller than the circumference of the overriding portion 22*b*, it is possible to inhibit an increase in the sliding resistance of the valve body 20 with respect to the accommodating concave portion 13 caused by the pressing portion 22*a*.

In the connector 1 according to this embodiment, because the spring body 30 that applies the biasing force to the valve body 20 from the opened position side toward the closed position side is arranged in the accommodating concave portion 13, it is possible to apply the biasing force to the valve body 20 by a simple configuration.

Because the connector 1 according to this embodiment is provided with the valve member V made of the elastic material integrally including the valve body 20 and the spring body 30, a configuration is made simple.

In the connector 1 according to this embodiment, the housing 10 is formed of the cap member C including the tubular body connecting unit 11 and the holder member H including the accommodating concave portion 13, and the internal flow path 12 includes the space defined between the cap member C and the holder member H, so that this has a configuration appropriate for mass production.

In the above-described embodiment, the overriding portion 22*b* has the ring-shape and is configured to serve as the seal portion. However, the shape of the overriding portion 22*b* and the inner peripheral surface 13*a* of the accommodating concave portion 13 is not limited to the ring-shape and it is only required that this is annular; for example, this may also be an elliptical shape, a polygonal shape such as a regular polygonal shape and a star polygonal shape and the like. Such an annular seal portion may also be provided on the valve body 20 apart from the overriding portion 22*b*. The overriding portion 22*b* and the receiving portion 13*a*2 are not limited to annular shapes, and may also be formed as at least one pair of convex and concave portions. It is not necessary that the overriding portion 22*b* is a convex portion and the receiving portion 13*a*2 is a concave portion. Rather, the overriding portion 22*b* may be a concave portion and the receiving portion 13*a*2 may be a convex portion.

Figure 7:
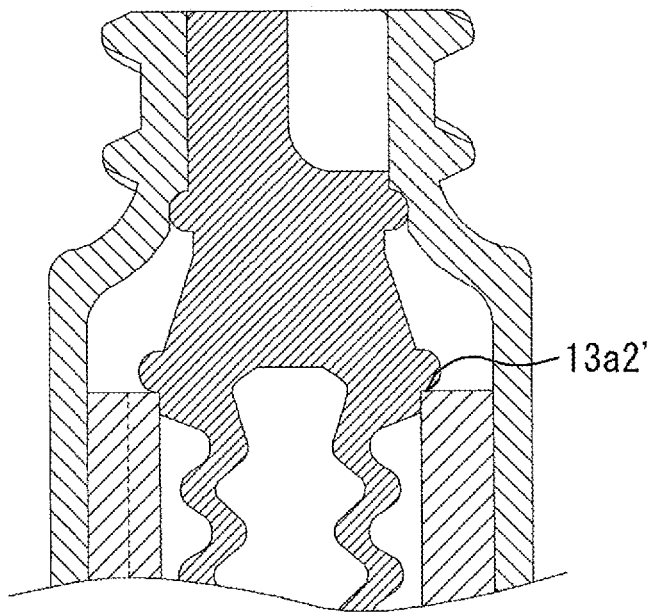
FIG. 7 is a cross-sectional view illustrating a variation of the connector according to an embodiment of the present invention according to FIG. 2.

In the embodiment described above, the inner peripheral surface 13*a* of the accommodating concave portion 13 includes the large-diameter portion 13*a*3 and the receiving portion 13*a*2 having the arc-shaped cross-sectional shape in the vertical direction. However, as illustrated in FIG. 7, for example, it is also possible that this includes not the large-diameter portion 13a3, but a receiving portion 13a2' having a linear cross-sectional shape in the vertical direction.

Figure 8:
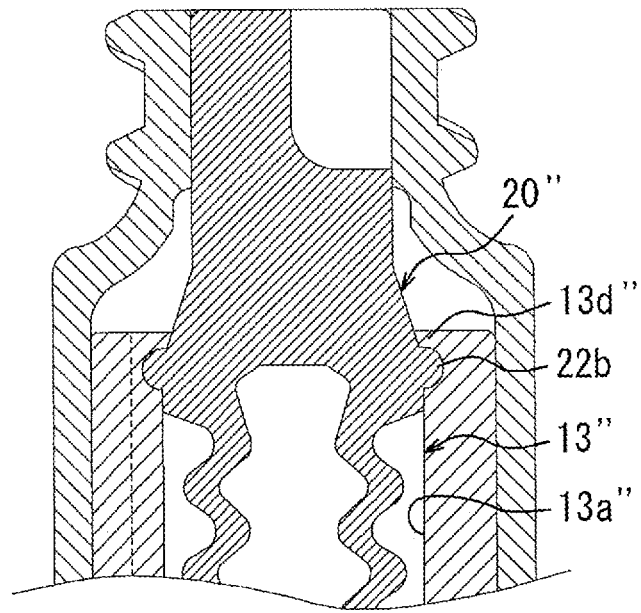
FIG. 8 is a cross-sectional view illustrating another variation of the connector according to an embodiment of the present invention according to FIG. 2.

In the above-described embodiment, the valve body 20 is provided with the pressing portion 22a serving as the ring-shaped seal portion. However, the shape of the pressing portion 22a and the second receiving portion 16 is not limited to the ring-shape as already described regarding the overriding portion 22b, and this may be an elliptical shape, a polygonal annular shape such as a regular polygonal shape and a star polygonal shape, and another shape, for example. As illustrated in FIG. 8, the pressing portion 22a may also be omitted. In this case, in order to inhibit occurrence of slip of a valve body 20", for example, it is possible to provide an annular convex portion 13d" that prevents upward movement of the overriding portion 22b on an upper end edge of an inner peripheral surface 13a" of an accommodating concave portion 13".

The description above merely illustrates exemplary embodiments of the present invention, and it goes without saying that the claims are not limited to the embodiments described above.

REFERENCE NUMERAL LIST

1 Connector
10 Housing
11 Tubular body connecting unit
11a Connecting opening
11b Male screw
12 Internal flow path
12a Annular flow path
12b Side flow path
12c Additional flow path
13, 13" Accommodating concave portion
13a, 13a" Inner peripheral surface
13a1 Small-diameter portion
13a2, 13a2' Receiving portion
13a3 Large-diameter portion
13b Bottom surface
13c Support column
13d" Annular convex portion
14 Connecting tubular body
14a Tubular portion
15 Ventilation path
15a First end
15b Second end
16 Second receiving portion
17 Support rib
20, 20" Valve body
21 Head portion
21a Slit
22 Body portion
22a Pressing portion
22b Overriding portion
30 Spring body
O Axis
T Tubular body
T1 Lumen
V Valve member
C Cap member
H Holder member

What is claimed is:

1. A connector comprising:
a housing comprising:
a tubular body connecting unit to which a tubular body is connectable, the tubular body connecting unit defining:
a connecting opening configured to receive the tubular body, and
an internal flow path configured to communicate with a lumen of the tubular body when the tubular body is connected to the tubular body connecting unit, and
a concave portion inside the housing, the concave portion having an inner peripheral surface comprising:
a small-diameter portion having a first diameter,
a large-diameter portion having a second diameter that is greater than the first diameter, and
a receiving portion extending from the small-diameter portion to the large-diameter portion; and
a valve body configured such that, when the tubular body is connected to the tubular body connecting unit, the valve body is pressed by the tubular body against a biasing force, thereby sliding on the inner peripheral surface of the concave portion from a closed position, in which communication of the internal flow path with an outside of the housing is interrupted, to an opened position, in which the internal flow path communicates with the lumen of the tubular body, wherein the valve body comprises:
a cylindrical head portion that closes the connecting opening when the valve body is in the closed position,
an overriding portion located below the cylindrical head portion and configured such that:
when the valve body is in the closed position, the overriding portion abuts the receiving portion at a location between the small-diameter portion and the large-diameter portion, and
as the valve body slides from the closed position toward the opened position, the overriding portion moves from the large-diameter portion to the small-diameter portion by riding over the receiving portion by elastic deformation, and
a pressing portion configured such that, as the valve body slides from the opened position to the closed position, the pressing portion is pressed against a second receiving portion provided on the housing.

2. The connector according to claim 1, wherein the overriding portion has an annular shape and comprises a seal portion, and the overriding portion is configured to slide on the inner peripheral surface of the concave portion as the valve body slides from the closed position toward the opened position.

3. The connector according to claim 2, wherein the overriding portion is an annular convex portion, and the receiving portion is an annular stepped portion.

4. The connector according to claim 1, wherein, in the closed position of the valve body, the pressing portion abuts the second receiving portion.

5. The connector according to claim 4, wherein:
the second receiving portion is continuous with the connecting opening; and
the pressing portion has an annular shape and comprises a second seal portion, and the pressing portion is configured such that, in the closed position of the valve body, the pressing portion abuts the second receiving portion in a liquid-tight manner.

6. The connector according to claim 5, wherein the pressing portion is an annular convex portion, and the second receiving portion is an annular stepped portion.

7. The connector according to claim 1, wherein:
the pressing portion is configured such that, as the valve body slides to the opened position, the pressing portion moves to an inside of the concave portion;
each of the pressing portion and the overriding portion is an annular convex portion; and
a circumference of the pressing portion is smaller than a circumference of the overriding portion.

8. The connector according to claim 7, wherein the circumference of the pressing portion is smaller than a circumference of the inner peripheral surface of the concave portion.

9. The connector according to claim 1, wherein a spring body is located in the concave portion, the spring body being configured to apply biasing force to the valve body from an opened position side toward a closed position side.

10. The connector according to claim 9, wherein the valve body and the spring body are integral parts of a valve member made of an elastic material.

11. The connector according to claim 1, wherein:
the housing comprises:
a cap member that comprises the tubular body connecting unit, and
a holder member; and
the internal flow path comprises a space defined between the cap member and the holder member.

12. The connector according to claim 11, wherein the holder member comprises the concave portion.

13. The connector according to claim 11, wherein the holder member comprises the small-diameter portion, the receiving portion, the large diameter portion, and an annular convex portion configured to inhibit the valve body from moving from the large-diameter portion away from the small-diameter portion.

14. The connector according to claim 1, wherein the concave portion inside the housing further comprises a bottom surface.

15. A connector comprising:
a housing comprising:
a cap member comprising a tubular body connecting unit to which a tubular body is connectable, the tubular body connecting unit defining:
a connecting opening configured to receive the tubular body, and
an internal flow path configured to communicate with a lumen of the tubular body when the tubular body is connected to the tubular body connecting unit, and
a holder member comprising a concave portion inside the housing, the concave portion having an inner peripheral surface comprising:
a small-diameter portion having a first diameter,
a large-diameter portion having a second diameter that is greater than the first diameter,
a receiving portion extending from the small-diameter portion to the large-diameter portion, and
an annular convex portion; and
a valve body configured such that, when the tubular body is connected to the tubular body connecting unit, the valve body is pressed by the tubular body against a biasing force, thereby sliding on the inner peripheral surface of the concave portion from a closed position, in which communication of the internal flow path with an outside of the housing is interrupted, to an opened position, in which the internal flow path communicates with the lumen of the tubular body, wherein the valve body comprises:
a cylindrical head portion that closes the connecting opening when the valve body is in the closed position, and
an overriding portion located below the cylindrical head portion and configured such that:
when the valve body is in the closed position, the overriding portion abuts the receiving portion at a location between the small-diameter portion and the large-diameter portion, and
as the valve body slides from the closed position toward the opened position, the overriding portion moves from the large-diameter portion to the small-diameter portion by riding over the receiving portion by elastic deformation,
wherein the internal flow path comprises a space defined between the cap member and the holder member,
wherein the annular convex portion is configured to inhibit the valve body from moving from the large-diameter portion away from the small-diameter portion.

* * * * *